United States Patent
Leeah et al.

(10) Patent No.: US 10,952,963 B2
(45) Date of Patent: Mar. 23, 2021

(54) READY TO USE LIQUID RECK FORMULATION

(71) Applicant: QuVa Pharma, Inc., Sugar Land, TX (US)

(72) Inventors: Travis A. Leeah, Sugar Land, TX (US); Jianping Chen, Sugar Land, TX (US)

(73) Assignee: QuVa Pharma, Inc., Sugar Land, TX (US)

( * ) Notice: Subject to any disclaimer, the term of this patent is extended or adjusted under 35 U.S.C. 154(b) by 100 days.

(21) Appl. No.: 16/381,446

(22) Filed: Apr. 11, 2019

(65) Prior Publication Data
US 2019/0314278 A1    Oct. 17, 2019

Related U.S. Application Data

(60) Provisional application No. 62/656,248, filed on Apr. 11, 2018.

(51) Int. Cl.
| | |
|---|---|
| *A61K 9/08* | (2006.01) |
| *A61P 29/02* | (2006.01) |
| *A61K 31/137* | (2006.01) |
| *A61K 31/407* | (2006.01) |
| *A61K 31/4168* | (2006.01) |
| *A61K 31/445* | (2006.01) |
| *A61K 47/02* | (2006.01) |
| *A61K 47/12* | (2006.01) |
| *A61K 47/18* | (2017.01) |
| *A61M 5/00* | (2006.01) |
| *A61K 9/00* | (2006.01) |

(52) U.S. Cl.
CPC .............. *A61K 9/08* (2013.01); *A61K 9/0019* (2013.01); *A61K 31/137* (2013.01); *A61K 31/407* (2013.01); *A61K 31/4168* (2013.01); *A61K 31/445* (2013.01); *A61K 47/02* (2013.01); *A61K 47/12* (2013.01); *A61K 47/183* (2013.01); *A61M 5/002* (2013.01); *A61P 29/02* (2018.01)

(58) Field of Classification Search
CPC combination set(s) only.
See application file for complete search history.

(56) References Cited

U.S. PATENT DOCUMENTS

| | | | | |
|---|---|---|---|---|
| 6,008,256 | A  * | 12/1999 | Haraguchi | ........... A61K 31/195 514/626 |
| 10,130,592 | B2 * | 11/2018 | Kannan | ..................... A61P 9/06 |
| 2003/0216413 | A1 | 11/2003 | Root-Bernstein et al. | |
| 2018/0000804 | A1 | 1/2018 | Berkeimer | |

FOREIGN PATENT DOCUMENTS

WO    2010139752 A2    12/2010

OTHER PUBLICATIONS

Connors, K.A., et al., "Epinephrine", Drug Kinetics, Chemical Stability of Pharmaceuticals, A Handbook for Pharmacists, Second Edition; pp. 438-447 (1986).
Naropin® (ropivacaine HCI) Injection prescribing information, Mar. 2012.
Ketorolac Tromethamine Injection, USP prescribing information, Hospira ANDA 074802, Dec. 2011.
Grubstein, B., and E. Milano, "Stabilization of Epinephrine in a Local Anesthetic Injectable Solution Using Reduced Levels of Sodium Metabisulfite and EDTA", Drug Development and Industrial Pharmacy, 18(14), 1549-1566 (1992).
Epipen® (epinephrine injection USP) prescribing information, Apr. 2017.
Duraclon® (clonidine hydrochloride) injection prescribing information, May 2010.
Dalury, D. F., et al., "Current and Innovative Pain Management Techniques in Total Knee Arthroplasty", Journal of Bone & Joint Surgery, 93A(20) pp. 1938-1943 (2011).
Toradol® oral tablets (ketorolac tromethamine tablets) prescribing information, Dec. 2008.
International Search Report and Written Opinion dated Jul. 9, 2019 in corresponding International Application No. PCT/US2019/026957.
Collis, Philip N., et al., "Periarticular Injection After Total Knee Arthroplasty Using Liposomal Bupivacaine vs a Modified Ranawat Suspension: A Prospective, Randomized Study", The Journal of Arthroplasty, 31(3): 633-636 (2015).
Kelley, Todd C., et al., "Efficacy of Multimodal Perioperative Analgesia Protocol with Periarticular Medication Injection in Total Knee Arthroplasty", The Journal of Arthroplasty, 28(8): 1274-1277 (2013).

\* cited by examiner

*Primary Examiner* — Kortney L. Klinkel
*Assistant Examiner* — Tori Strong
(74) *Attorney, Agent, or Firm* — Daniel R. Evans; Melissa M. Hayworth

(57) ABSTRACT

Disclosed herein is a ready-to-use liquid formulation comprising ropivacaine, epinephrine, clonidine, and ketorolac (collectively referred to as RECK). Also disclosed herein is a process for preparing the RECK-containing liquid formulation, as well as methods for using the same.

19 Claims, No Drawings

READY TO USE LIQUID RECK FORMULATION

RELATED APPLICATION

The present application claims priority to U.S. Provisional Patent Application No. 62/656,248, filed on Apr. 11, 2018, herein incorporated by reference in its entirety.

FIELD OF THE INVENTION

Disclosed herein is a ready-to-use liquid formulation comprising ropivacaine, epinephrine, clonidine, and ketorolac (collectively referred to as RECK). Also disclosed herein is a process for preparing the RECK-containing liquid formulation, as well as methods for using the same.

BACKGROUND

The surgical reconstruction or replacement of a joint, known as arthroplasty, may be necessary to alleviate pain associated with osteoarthritis. A problem associated with arthroplasty is the management of post-operative pain. Indeed, it is generally recognized that failure to control pain adequately following an arthroplasty procedure may hinder physiotherapy and increase anxiety.

A RECK-containing solution may be used as a local anesthetic during an arthroplasty procedure. In fact, some hospitals use a RECK-containing solution during knee arthroplasty to improve immediate post-operative pain relief. See, e.g., Dalury et al., *Current and Innovative Pain Management Techniques in Total Knee Arthoroplasty*, JBJS (2011) 93(20): 1938-1943 (Dulury). Therein, Dulury describes an "anesthetic cocktail" containing ropivacaine, epinephrine, clonidine, and ketorolac in saline prepared from commercially available products. (Dulury at 1941.) Dulury describes the use of the anesthetic cocktail for patients during total knee replacement to improve immediate post-operative pain. (Id. at 1941-1942.) Dulury explains that the anesthetic cocktail "is premixed by the pharmacy and remains stable for twenty-four hours." (Id.)

In addition to the limited stability of the compounded RECK-containing solution, pharmacy preparation of a RECK-containing solution has the potential for microbial contamination and/or errors associated with compounding. Indeed, hospital personnel have stated that the RECK-containing solution sometimes turn pink, which is a sign of epinephrine degradation. There is a need for a ready-to-use liquid formulation containing RECK that overcomes the problems of the RECK-containing solution to ensure that patients have decreased pain during rehabilitation post-operative arthroplasty.

DETAILED DESCRIPTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not.

A first embodiment is directed to a ready-to-use liquid formulation comprising: ropivacaine hydrochloride in an amount of about 2.5 mg/mL; epinephrine hydrochloride in an amount of about 5 mcg/mL, based on epinephrine free base; clonidine hydrochloride in an amount of about 0.8 mcg/mL; ketorolac tromethamine in an amount of about 0.3 mg/mL; sodium chloride in an amount of about 8.5 mg/mL; sodium metabisulfite in an amount of about 2.6 mcg/mL; ethylenediaminetetraacetic acid ("EDTA") sodium in an amount of about 0.2 mg/mL; optionally citric acid in an amount of about 2 mg/mL; a sufficient amount of sterile water for injection; and a sufficient amount of a pH adjuster to obtain a pH of from about 4.6 to about 4.9.

In a first aspect of the first embodiment, the citric acid is present in the formulation in an amount of about 2 mg/mL.

In a second aspect of the first embodiment, the ready-to-use liquid formulation does not contain citric acid.

In a third aspect of the first embodiment, the pH is about 4.7 to about 4.8.

In a fourth aspect of the first embodiment, the pH adjuster is hydrochloric acid, sodium hydroxide, or a combination thereof.

In a fifth aspect of the first embodiment, the ready-to-use liquid formulation may be stored within a light-resistant container having a light transmission of less than 5%, less than 4%, less than 3%, less than 2%, or less than 1% at any wavelength between 290 nm and 450 nm. Said light-resistant container may comprise, for example, an amber-colored bag, film, or plastic.

A second embodiment is directed to a syringe comprising any one of the ready-to-use liquid formulations of the first embodiment. Stability tests of the syringed formulations show that each of ropivacaine, epinephrine, clonidine, and ketorolac has a potency of at least 90% after storage for about 90 days at a temperature of about 25° C.

In a first aspect of the second embodiment, each of ropivacaine, epinephrine, clonidine, and ketorolac has a potency of at least 90% after storage for about 90 days at a temperature of about 25° C.

In a second aspect of the second embodiment, the syringe comprises about 50 mL of the ready-to-use formulation.

A third embodiment is directed to a light-sensitive container comprising any one of the syringes of the second embodiment, wherein the light-sensitive container has a light transmission of less than 5%, less than 4%, less than 3%, less than 2%, or less than 1% at any wavelength between 290 nm and 450 nm. Said light-sensitive container may comprise, for example, an amber-colored film or an amber-colored plastic.

A fourth embodiment is directed to a ready-to-use liquid formulation consisting of: ropivacaine hydrochloride in an amount of about 2.5 mg/mL; epinephrine hydrochloride in an amount of about 5 mcg/mL, based on epinephrine free base; clonidine hydrochloride in an amount of about 0.8 mcg/mL; ketorolac tromethamine in an amount of about 0.3 mg/mL; sodium chloride in an amount of about 8.5 mg/mL; sodium metabisulfite in an amount of about 2 mcg/mL to about 10 mcg/mL; EDTA sodium in an amount of about 0.2 mg/mL; optionally citric acid in an amount of about 2 mg/mL; a sufficient amount of sterile water for injection; and a sufficient amount of a pH adjuster to obtain a pH of from about 4.6 to about 4.9.

In a first aspect of the fourth embodiment, the citric acid is present in the formulation in an amount of about 2 mg/mL.

In a second aspect of the fourth embodiment, the ready-to-use liquid formulation does not contain citric acid.

In a third aspect of the fourth embodiment, the pH is about 4.7 to about 4.8.

In a fourth aspect of the fourth embodiment, the pH adjuster is hydrochloric acid, sodium hydroxide, or a combination thereof.

In a fifth aspect of the fourth embodiment, the ready-to-use liquid formulation may be stored within a light-resistant container having a light transmission of less than 5%, less than 4%, less than 3%, less than 2%, or less than 1% at any wavelength between 290 nm and 450 nm. Said light-resistant container may comprise, for example, an amber-colored bag, film, or plastic.

A fifth embodiment is directed to a syringe comprising any one of the ready-to-use liquid formulations of the fourth embodiment. Stability tests of the syringed formulations show that each of ropivacaine, epinephrine, clonidine, and ketorolac has a potency of at least 90% after storage for 90 days at a temperature of about 25° C.

In a first aspect of the fifth embodiment, each of ropivacaine, epinephrine, clonidine, and ketorolac has a potency of at least 90% after storage for about 90 days at a temperature of about 25° C.

In a second aspect of the fifth embodiment, the syringe comprises about 50 mL of the ready-to-use formulation.

A sixth embodiment is directed to a light-sensitive container comprising any one of the syringes of the fifth embodiment, wherein the light-sensitive container has a light transmission of less than 5%, less than 4%, less than 3%, less than 2%, or less than 1% at any wavelength between 290 nm and 450 nm. Said light-sensitive container may comprise, for example, an amber-colored film or an amber-colored plastic.

A seventh embodiment is directed to a method for alleviating post-operative pain in a patient in need thereof, which comprises: administering to the patient any one of the ready-to-use liquid formulations described in the first through sixth embodiments.

In a first aspect of the seventh embodiment, the patient receives arthroplasty treatment of the knee, hip, or other joint.

In a second aspect of the seventh embodiment, the patient the arthroplasty treatment is knee replacement surgery. As explained in Dulury, a total volume of 100 mL is used, in which 25 mL is injected into each of the: (i) posterior capsule, (ii) medial periosteum and medial capsule, (iii) lateral periosteum and lateral capsules, and (iv) soft tissues around the skin incision.

An eighth embodiment is directed to the ready-to-use liquid formulation of any embodiments one through six for use in the treatment for alleviating post-operative pain in a patient in need thereof.

A ninth embodiment is directed to a process for preparing any one of the ready-to-use liquid formulation of embodiments one through six, which comprises (or consists of): a) adding sodium metabisulfite and EDTA Sodium in a first container including sterile water for injection and stirring to provide a dissolved solution; b) adding 10% v/v hydrochloric acid to the first container of step a) to obtain a pH of about 2.5; c) dissolving epinephrine free base to the first container of step b); d) if necessary, adding 10% v/v hydrochloric acid to the first container of step c) to maintain the pH of the solution below 3.0; e) adding an additional amount of sterile water to the first container of step d) and adding the pH adjuster to obtain a pH of from about 4.0 to obtain an epinephrine solution; f) dissolving sodium chloride and ropivacaine hydrochloride in a vessel containing sterile water for injection; g) adding the pH adjuster to the vessel of step f) to obtain a pH that ranges from about 4.6 to about 4.9; h) adding separately clonidine hydrochloride, ketorolac tromethamine, and the epinephrine solution of step e) to the vessel; i) adding an additional amount of sterile water to the vessel of step h) and adding the pH adjuster to obtain a pH that ranges from about 4.6 to about 4.9; j) transferring the solution of step i) to a second container; and k) filtering the solution of step j) through a 0.22 micron filter.

A tenth embodiment is directed to a syringe product comprising the ready-to-use liquid formulation prepared by the process of the sixth embodiment. Stability tests of the syringed formulations show that each of ropivacaine, epinephrine, clonidine, and ketorolac has a potency of at least 90% after storage for 90 days at a temperature of about 25° C.

In a first aspect of the tenth embodiment, each of ropivacaine, epinephrine, clonidine, and ketorolac has a potency of at least 90% after storage for about 90 days at a temperature of about 25° C.

In a second aspect of the tenth embodiment, each of ropivacaine, epinephrine, clonidine, and ketorolac has a potency of at least 90% after storage for 90 days at a temperature of about 25° C.

In a third aspect of the tenth embodiment, the syringe comprises about 50 mL of the ready-to-use formulation.

An eleventh embodiment is directed to a light-sensitive container comprising any one of the syringes of the tenth embodiment, wherein the light-sensitive container has a light transmission of less than 5%, less than 4%, less than 3%, less than 2%, or less than 1% at any wavelength between 290 nm and 450 nm. Said light-sensitive container may comprise, for example, an amber-colored bag, film, or plastic.

EXAMPLES

BD syringes described herein are available commercially from Becton, Dickinson and Company. The BD syringes are fitted with a Luer-Lok tip and have volumes (in mL) of: 1, 3, 5, 10, 20, 30, and 60.

Ultra Performance Liquid Chromatography (UPLC) was used for purposes of identification and potency determinations.

|  | Epinephrine and Clonidine | Ropivacaine and Ketorolac |
|---|---|---|
| Equipment: | Waters Acquity H Class UPLC with UV Detector (or equivalent) | Waters Acquity H Class UPLC with UV Detector (or equivalent) |
| Column: | Luna 5 μm C18(2) 100A, 150 × 4.6 mm column | Luna 5 μm C18(2) 100A, 150 × 4.6 mm column |
| Column Temperature: | 30.0° C. | 50.0° C. |
| Flow Rate: | 1.0 mL/min | 0.5 mL/min |
| Injection Volume: | 10 μL | 1 μL |
| UV Detector: | 220 nm | 254 nm |
| Run Time: | 30 minutes | About 20 minutes |

|  | Epinephrine and Clonidine | Ropivacaine and Ketorolac |
| --- | --- | --- |
| Seal Wash, Purge, and Wash: | 50:50 Water:Methanol | 50:50 Water:Methanol |
| Mobile Phase A: | pH 3.0 buffer | pH 3.0 buffer |
| Mobile phase B: | Methanol:Acetonitrile 250:50 | Methanol |
| Gradient: | 0.0 min: 75.0% A\|25.0% B<br>6.0 min: 70.0% A\|30.0% B<br>15.0 min: 50.0% A\|50.0% B<br>20.0 min: 20.0% A\|80.0% B<br>25.0 min: 70.0% A\|30.0% B<br>30.0 min: 70.0% A\|30.0% B | N.A. Isocratic: 65% A\|35% B |

Phosphate Buffer Preparation (for Epinephrine and Clonidine): Dissolve 1.1 g of 1-Heptanesulfonic acid Sodium Salt in 1000 mL of purified water and mix well. Adjust the pH of the buffer with Phosphoric acid to pH 3.0.

Phosphate Buffer Preparation (for Ropivacaine and Ketorolac): Dissolve 1.4 g of Potassium Phosphate Monobasic in 1000 mL of purified water and mix well. Adjust the pH of the buffer with Phosphoric acid to pH 3.0.

Potency assays used standard solutions of each API and working standards solutions that contain (i) epinephrine and clonidine HCl and (ii) Ropivacaine HCl and Ketorolac Tromethamine.

The concentration of working standard solution is about 5 mcg/ml for Epinephrine base and about 0.8 mcg/ml for Clonidine HCl. The standard stock solution for epinephrine used epinephrine bitartrate, while the standard stock solution for clonidine used either clonidine free base or clonidine HCl.

The concentration of Ropivacaine HCl in the working standard solution is about 0.25 mg/ml, while the concentration of Ketorolac Tromethamine is about 0.03 mg/ml.

Calculate the Potency of Ropivacaine HCl as Follows:

$$\text{Ropivacaine HCl Potency (\%)} = \frac{As}{Astd} \times C \times \frac{P}{100} \times DF \times \frac{1}{LC} \times 100$$

Where

As is the UPLC peak area of ropivacaine (elution time of 3.81 min);

Astd is the average UPLC peak area (N=5) of ropivacaine from working standard solution;

C is the working standard concentration of Ropivacaine HCl, about 0.25 mg/mL;

P is the Standard potency, % (obtained by comparison to standard solution);

DF is a dilution factor (100.0 mL/10.00 mL); and

LC is the Label Claim of the Ropivacaine HCl in the RECK composition, 2.46 mg/mL.

Calculate the Potency of Epinephrine as Follows:

$$\text{Epinephrine Potency (\%)} = \frac{As}{Astd} \times C \times \frac{P}{100} \times \frac{1}{LC} \times CF \times 100$$

Where

As is the UPLC peak area of epinephrine (elution time of 5.57 min);

Astd is the average UPLC peak area (N=5) of epinephrine from working standard solution;

C is the working standard solution concentration of Epinephrine Bitartrate, about 5 mcg/mL;

P is the standard potency, % (obtained by comparison to standard solution);

CF is the correction factor (0.54969), which is the ratio of the molecular weight of epinephrine (183.207) to the molecular weight of epinephrine bitartrate (333.29); and LC is the Label Claim of the Epinephrine base in RECK composition, 5.0 mcg/mL.

Calculate the Potency of Clonidine HCl as Follows:

$$\text{Clonidine HCl Potency (\%)} = \frac{As}{Astd} \times C \times \frac{P}{100} \times \frac{1}{LC} \times CF \times 100$$

Where

As is the UPLC peak area of clonidine (elution time of 14.65 min);

Astd is the average UPLC peak area (N=5) of clonidine from working standard solution;

C is the Standard concentration of Clonidine or Clonidine HCl, about 0.8 mcg/mL

P is the Standard potency, % (obtained by comparison to standard solution);

CF (applicable only if a Clonidine standard is used) is the correction factor (1.15844), which is the ratio of the molecular weight of Clonidine HCl (266.55) to the molecular weight of Clonidine (230.093) (N.B.; CF is not applicable if Clonidine HCl standard is used.)

LC is the Label Claim of Clonidine HCl in the RECK composition, 0.8 mcg/ml of Clonidine HCl Calculate the Potency of Ketorolac Tromethamine as Follows:

$$\text{Ketorolac Tromethamine Potency (\%)} = \frac{As}{Astd} \times C \times \frac{P}{100} \times DF \times \frac{1}{LC} \times 100$$

Where

As is the UPLC peak area of Ketorolac Tromethamine (elution time of 14.89 min);

Astd is the average UPLC peak area (N=5) of Ketorolac Tromethamine from working standard solution;

C is the Standard concentration of Ketorolac Tromethamine, mg/ml

P is the Standard potency, % (obtained by comparison to standard solution)

DF is a dilution factor (100.0 mL/10.00 mL); and

LC is the Label Claim of Ketorolac Tromethamine in the RECK composition, 0.3 mg/mL.

It was discovered that the RECK components exhibit inherent incompatibilities. For instance, each of ropivacaine, epinephrine, and clonidine exhibits maximum stability at a pH range of 3-4, while ketorolac exhibits maximum stability at a pH range of 6-7. Epinephrine undergoes substantial degradation at a pH greater than 4. The rate of epinephrine degradation correlates directly with aerial exposure and to some degree by light exposure. The rate of ketorolac degradation increases at a pH less than 5.

Multiple antioxidants, chelating agents, and buffers were evaluated to stabilize both epinephrine and ketorolac, which include: sodium bisulfite, sodium metabisulfite, EDTA Sodium Dihydrate (i.e., EDTA Sodium), citric acid, sodium phosphate dibasic, and PEG 400. Solution pH values were evaluated from a pH of 3.9-6.0. After extensive testing, it was determined that a pH of about 4.8 provides for acceptable stability of both epinephrine and ketorolac.

In theory, multiple antioxidants in combination with a buffer could be used to stabilize epinephrine, said combinations include, sodium phosphates, citric acid, and sodium metabisulfite (at 1 mg/mL or higher or in combination with buffers). Based on the evaluation of numerous compositions, it was discovered that ketorolac degrades substantially in the presence of sodium metabisulfite at a concentration of 1 mg/mL or higher and that epinephrine also degrades in a relatively short period of time. It was also discovered that buffers are ineffective in stabilizing ketorolac and that ketorolac tended to degrade at a pH less than about 4.5.

Naropin® (ropivacaine HCl) Injection is a sterile, isotonic solution that contains the enantiomerically pure drug substance, sodium chloride for isotonicity and water for injection available in single dose containers in 2 (0.2%), 5 (0.5%), 7.5 (0.75%) and 10 mg/mL (1%) concentrations. The specific gravity of Naropin Injection solutions range from 1.002 to 1.005 at 25° C.

EpiPen® (epinephrine injection, USP) contains epinephrine (1 mg/mL), sodium chloride (6 mg/mL), sodium metabisulfite (1.7 mg/mL), hydrochloric acid to adjust pH to 2.2-5.0, and water for injection.

Duraclon® (clonidine hydrochloride) Injection is supplied as a clear, colorless, preservative-free, pyrogen-free, aqueous sterile solution (pH 5 to 7) in single-dose, 10 mL vials. Each mL of the 100 μg/mL (0.1 mg/mL) concentration contains 100 μg of Clonidine Hydrochloride, USP and 9 mg Sodium Chloride, USP in Water for Injection, USP. Hydrochloric Acid and/or Sodium Hydroxide may have been added for pH adjustment. Each 10 mL vial contains 1 mg (1000 μg) of clonidine hydrochloride.

Ketorolac Tromethamine Injection, USP is available for intravenous (IV) or intramuscular (IM) administration as: 15 mg in 1 mL (1.5%) and 30 mg in 1 mL (3%) in sterile solution; 60 mg in 2 mL (3%) of ketorolac tromethamine in sterile solution is available for IM administration only. The solutions contain 10% (w/v) alcohol, USP, and 6.68 mg, 4.35 mg, and 8.70 mg, respectively, of sodium chloride in sterile water. The pH range is 6.9 to 7.9 and is adjusted with sodium hydroxide and/or hydrochloric acid.

Examples 1-6. Evaluation of Epinephrine Content with Varying Amounts of Sodium Metabisulfite with or without Sodium EDTA Considering that ketorolac rapidly decomposes in the presence of 1 mg/mL or more of sodium metabisulfite, the following compositions were prepared using varying concentrations of sodium metabisulfite with or without sodium EDTA. (The stated concentration of epinephrine hydrochloride (5 mcg/mL) is based on the concentration of epinephrine free base.)

|  | Examples | | | | | |
| --- | --- | --- | --- | --- | --- | --- |
|  | 1 | 2 | 3 | 4 | 5 | 6 |
| Ropivacaine HCl (mg/mL) | 2.46 | 2.46 | 2.46 | 2.46 | 2.46 | 2.46 |
| Epinephrine HCl (mcg/mL) | 5 | 5 | 5 | 5 | 5 | 5 |
| Clonidine HCl (mcg/mL) | 0.8 | 0.8 | 0.8 | 0.8 | 0.8 | 0.8 |
| Ketorolac Tromethamine (mg/mL) | 0.3 | 0.3 | 0.3 | 0.3 | 0.3 | 0.3 |
| Sodium Chloride (mg/mL) | 8.5 | 8.5 | 8.5 | 8.5 | 8.5 | 8.5 |
| Sodium Metabisulfite (mcg/mL) | 2.06 | 2.58 | 5.515 | 7.21 | 10.3 | 2.58 |
| EDTA Sodium (mg/mL) | — | — | — | — | — | 0.2 |
| 10% w/v HCl and/or 10% w/v NaOH | q.s. (pH 4.6-4.9) | | | | | |
| SWFI | q.s. | | | | | |
| Epinephrine Potency (%) | | | | | | |
| Day 3, 5° C. | 96 | 95.2 | 95.1 | 95.1 | 92.3 | 98.9 |
| Day 3, 25° C. | 91.6 | 90.1 | 82.5 | 90.9 | 85.7 | 98.5 |
| Day 3, 40° C. | 71.8 | 94.8 | 70.3 | 72.7 | 67.1 | 97.6 |
| Day 3, 70° C. | 5.7 | 3.4 | 1.8 | 4.5 | 1.1 | 76.4 |

The compositions were stored at four different temperatures (5° C., 25° C., 40° C., and 70° C.) in a BD syringe, and were evaluated by UPLC for epinephrine potency after the third day of manufacture. The tabulated results show that the Example 6 composition exhibited the greatest degree of epinephrine potency for each temperature after three-days of storage. Indeed, storage of the Example 6 composition (for 30-days at 25° C.) showed an epinephrine potency of 94.3%. Surprisingly, the Example 6 composition showed a ketorolac potency of 102.3% (for 30 days at 25° C.). Based on these and other assays, it was determined that the Example 6 composition has a suitable shelf life (or Beyond Use Date) of about 90-days at 25° C.

The shelf life of about 90-days (25° C.) is surprising considering that no effort was made to exclude air from the RECK compositions. This is surprising since epinephrine oxidizes to adrenochrome in the presence of air. This also is surprising considering that dissolved oxygen may be present in water in an amount of about 9 mg/L, which corresponds to a molar amount of oxygen that exceeds the molar amount of epinephrine by about 10-fold.

Examples 7-8. Evaluation of RECK Compositions with and without Citric Acid

|  | Examples | |
| --- | --- | --- |
|  | 7 | 8 |
| Ropivacaine HCl (mg/mL) | 2.460 | 2.460 |
| Epinephrine HCl (mcg/mL) | 5 | 5 |
| Clonidine HCl (mcg/mL) | 0.8 | 0.8 |

-continued

| | Examples | |
|---|---|---|
| | 7 | 8 |
| Ketorolac Tromethamine (mg/mL) | 0.3 | 0.3 |
| Sodium Chloride (mg/mL) | 8.5 | 8.5 |
| Sodium Metabisulfite (mcg/mL) | 2.58 | 2.58 |
| EDTA Sodium (mg/mL) | 0.2 | 0.2 |
| Citric Acid (mg/mL) | 0.2 | — |
| 10% w/v HCl and/or 10% w/v NaOH | q.s. (pH 4.6-4.9) | q.s. (pH 4.6-4.9) |
| SWFI | q.s. | q.s |

| | API Potency (%) | | | | API Potency (%) | | | |
|---|---|---|---|---|---|---|---|---|
| | R | E | C | K | R | E | C | K |
| Day 3, 5° C. | 100.6 | 100.5 | 95.5 | 97.2 | 100.1 | 94.6 | 93.1 | 96.7 |
| Day 3, 25° C. | 99.4 | 100.0 | 97.0 | 94.3 | 99.8 | 94.4 | 94.3 | 96.3 |
| Day 30, 5° C. | 102.0 | 100.4 | 98.4 | 98.6 | 101.2 | 95.3 | 99.2 | 97.0 |
| Day 30, 25° C. | 100.3 | 98.9 | 96.8 | 93.6 | 101.1 | 93.8 | 96.6 | 93.8 |

The compositions were stored at four different temperatures (5° C., 25° C., 40° C., and 70° C.) in a BD syringe, and were evaluated by UPLC for API potency at various points in time. The measured potency for each active after storage for 30-days at either 5° C. or 25° C. shows that the compositions are stable.

Example 9: Preparation of Ready-to-Use Liquid Formulation Containing RECK

1. Prepare of Epinephrine solution
    1.1 Wrap a container (250 mL beaker) with amber bag for light protection. Add 120 mL of SWFI in the container.
    1.2 Add Sodium Metabisulfite (10.88 mg), as a powder or adding a sufficient amount of a sodium metabisulfite stock solution to the container to provide for a final sodium metabisulfite concentration of about 2.6 mcg/mL. The sodium metabisulfite stock solution as a concentration of, for example, 2.295 mg/mL.
    1.3 Add EDTA Sodium (0.840 g) to the container.
    1.4 Stir to dissolve the Sodium Metabisulfite and/or EDTA Sodium.
    1.5 Adjust pH to 2.5 using 10% HCl.
    1.6 Add Epinephrine (21.0 mg)
    1.7 Mix to dissolve Epinephrine powder for 90 min.
    1.8 Check pH and ensure the pH is below 3.0. If necessary, add a sufficient amount of 10% HCl to maintain a pH below 3.0.
    1.9 QS to 140 mL with SWFI and adjust pH to 4.0.
    1.10 QS to 150 mL with SWFI.

2. Wrap a vessel (mixing jug>5 L) with an amber bag for light protection. Add 3000 mL SWFI in the jug.
3. Add Sodium Chloride (35.7 g) and Ropivacaine HCl (10.33 g) to the vessel and stir for 15-30 minutes to dissolve Sodium Chloride and Ropivacaine HCl.
4. Adjust pH to 4.75 using 10% HCl and/or 10% NaOH.
5. Add following API solutions to the vessel with constant stirring.
    a. Measure 33.6 mL of 100 mcg/mL (3.36 mg) Clonidine HCl from commercial vial by a 60 mL syringe.
    b. Measure 42 mL of 30 mg/mL (1.26 g) Ketorolac Tromethamine injection from commercial vial by a 60 mL syringe.
    c. Add Epinephrine (150 mL) solution from Step 1; rinse container well and ensure all Epinephrine solution is transferred.
6. QS to 3800 ml (90% final volume) with SWFI.
7. Adjust the solution to pH 4.75.
10. QS to 4200 mL with SWFI. Mixing for 5 minutes.
11. Transfer 3100 mL into 3 L bag (protected from light).
12. Filter the solution using polyether sulfone (PES) filter (0.22 μm).
13. Fill 50 mL of solution in each 60 mL BD syringe with Luer-Lok tip (available commercially from Becton, Dickinson and Company).
14. Protect syringe product from light and store at room temperature (25° C.) or refrigerated (5-8° C.).

The syringe may be protected from light by storage in a container having a light transmission of less than 5%, less than 4%, less than 3%, less than 2%, or less than 1% at any wavelength between 290 nm and 450 nm. Said container may comprise, for example, an amber-colored film or an amber-colored plastic. (See, e.g., USP 40<671> for a procedure for determining spectral transmission of a container.)

The syringed products are tested for potency, stability, sterility, and endotoxin content, as shown below.

| Analysis | Specification | Test Method |
|---|---|---|
| Potency | 90.0-110.0%. for all 4 APIs (Ropivacaine, Epinephrine, Clonidine and Ketorolac) | Potency/Purity Analytical Testing Method (see UPLC methods) |
| Stability | API concentration lost within 10% from Day-0 | Concentration test by UPLC (see UPLC methods) |
| Sterility[1] | Sterile | USP <71> |
| Endotoxin | ≤0.148 EU/mL | USP <85> |

Sterility[1]: it meets or exceeds USP <71> requirements. Where no microorganism growth, test result is reported as "Sterile"; otherwise, report the detected microorganism colony forming units (CFU).

The potency (expressed as a percentage of the label claim) for each of ropivacaine, epinephrine, clonidine, and ketorolac was determined in syringe products (protected from light) initially and after 90-days after storage at a temperature of about 25° C. The following table summarizes the results for three products.

| | | 1 | | | | 2 | | | | 3 | | | |
|---|---|---|---|---|---|---|---|---|---|---|---|---|---|
| Potency | Td | R | E | C | K | R | E | C | K | R | E | C | K |
| % L.C. | 0 | 96.9 | 96.6 | 97.8 | 96.7 | 99.7 | 100. | 106.2 | 98.6 | 100.6 | 100.1 | 106.3 | 99.5 |
| | 90 | 97.9 | 95.7 | 97.9 | 93.6 | 100.3 | 99.3 | 101.8 | 95 | 100.2 | 98.1 | 101.3 | 95.8 |

The potency test results show that the ready-to-use formulation has a stability such that each of ropivacaine, epinephrine, clonidine, and ketorolac has a potency of at least 90% after storage for about 90-days at a temperature of about 25° C. The products also exhibited an endotoxin level of less than 0.10 EU/mL and passed sterility tests.

The subject matter of U.S. Provisional Patent Application No. 62/656,248, filed on Apr. 11, 2018, is incorporated by reference. Information disclosed in the related application and the references cited herein is incorporated by reference in its entirety. In the event that information incorporated by reference conflicts with the meaning of a term or an expression disclosed herein, the meaning of the term or the expression disclosed herein controls.

The invention claimed is:

1. A ready-to-use liquid formulation comprising:
   ropivacaine hydrochloride in an amount of about 2.5 mg/mL;
   epinephrine hydrochloride in an amount of about 5 mcg/mL, based on epinephrine free base;
   clonidine hydrochloride in an amount of about 0.8 mcg/mL;
   ketorolac tromethamine in an amount of about 0.3 mg/mL;
   sodium chloride in an amount of about 8.5 mg/mL;
   sodium metabisulfite in an amount of about 2.6 mcg/mL;
   EDTA sodium in an amount of about 0.2 mg/mL;
   optionally citric acid in an amount of about 2 mg/mL;
   a sufficient amount of sterile water for injection; and
   a sufficient amount of a pH adjuster to obtain a pH of from about 4.6 to about 4.9.

2. The ready-to-use liquid formulation of claim 1, wherein citric acid is present in the formulation in an amount of about 2 mg/mL.

3. The ready-to-use liquid formulation of claim 1, wherein the pH is about 4.7 to about 4.8.

4. The ready-to-use liquid formulation of claim 1, wherein the pH adjuster is hydrochloric acid, sodium hydroxide, or a combination thereof.

5. A syringe comprising about 50 mL of the ready-to-use liquid formulation of claim 1.

6. The syringe of claim 5, wherein each of ropivacaine, epinephrine, clonidine, and ketorolac has a potency of at least 90% after storage for about 90 days at a temperature of about 25° C.

7. A light-sensitive container comprising the syringe of claim 5, wherein the light-sensitive container has a light transmission of less than 5% at any wavelength between 290 nm and 450 nm.

8. A ready-to-use liquid formulation consisting of:
   ropivacaine hydrochloride in an amount of about 2.5 mg/mL;
   epinephrine hydrochloride in an amount of about 5 mcg/mL, based on epinephrine free base;
   clonidine hydrochloride in an amount of about 0.8 mcg/mL;
   ketorolac tromethamine in an amount of about 0.3 mg/mL;
   sodium chloride in an amount of about 8.5 mg/mL;
   sodium metabisulfite in an amount of about 2 mcg/mL to about 10 mcg/mL;
   EDTA sodium in an amount of about 0.2 mg/mL;
   optionally citric acid in an amount of about 2 mg/mL;
   a sufficient amount of sterile water for injection; and
   a sufficient amount of a pH adjuster to obtain a pH of from about 4.6 to about 4.9.

9. The ready-to-use liquid formulation of claim 8, wherein citric acid is present in the formulation in an amount of about 2 mg/mL.

10. The ready-to-use liquid formulation of claim 8, wherein the pH is about 4.7 to about 4.8.

11. The ready-to-use liquid formulation of claim 8, wherein the pH adjuster is hydrochloric acid, sodium hydroxide, or a combination thereof.

12. A syringe comprising about 50 mL of the ready-to-use liquid formulation of claim 8.

13. The syringe of claim 12, wherein each of ropivacaine, epinephrine, clonidine, and ketorolac has a potency of at least 90% after storage for about 90 days at a temperature of about 25° C.

14. A light-sensitive container comprising the syringe of claim 12, wherein the light-sensitive container has a light transmission of less than 5% at any wavelength between 290 nm and 450 nm.

15. A method for alleviating post-operative pain in a patient in need thereof, which comprises:
   administering the ready-to-use liquid formulation of claim 1 to the patient.

16. A process for preparing the ready-to-use liquid formulation of claim 1, which comprises:
   a) adding sodium metabisulfite and EDTA Sodium in a first container including sterile water for injection and stirring to provide a dissolved solution;
   b) adding 10% v/v hydrochloric acid to the first container of step a) to obtain a pH of about 2.5;
   c) dissolving epinephrine free base to the first container of step b);
   d) optionally, adding 10% v/v hydrochloric acid to the first container of step c) to maintain the pH of the solution below 3.0;
   e) adding an additional amount of sterile water to the first container of step d) and adding the pH adjuster to obtain a pH of from about 4.0 to obtain an epinephrine solution;
   f) dissolving sodium chloride and ropivacaine hydrochloride in a vessel containing sterile water for injection;
   g) adding the pH adjuster to the vessel of step f) to obtain a pH that ranges from about 4.6 to about 4.9;
   h) adding separately clonidine hydrochloride, ketorolac tromethamine, and the epinephrine solution of step e) to the vessel;
   i) adding an additional amount of sterile water to the vessel of step h) and adding the pH adjuster to obtain a pH that ranges from about 4.6 to about 4.9;
   j) transferring the solution of step i) to a second container; and
   k) filtering the solution of step j) through a 0.22-micron filter.

17. A syringe comprising about 50 mL of the ready-to-use liquid formulation prepared by the process of claim 16.

18. The syringe of claim 17, wherein each of ropivacaine, epinephrine, clonidine, and ketorolac has a potency of at least 90% after storage for about 90 days at a temperature of about 25° C.

19. A light-sensitive container comprising the syringe of claim 17, wherein the light-sensitive container has a light transmission of less than 5% at any wavelength between 290 nm and 450 nm.

* * * * *